(12) United States Patent
Niazi

(10) Patent No.: US 6,235,314 B1
(45) Date of Patent: May 22, 2001

(54) ANALGESIC, ANTI-INFLAMMATORY AND SKELETAL MUSCLE RELAXANT COMPOSITIONS

(76) Inventor: Sarfaraz K. Niazi, 20 Riverside Dr., Deerfield, IL (US) 60015

( * ) Notice: Subject to any disclaimer, the term of this patent is extended or adjusted under 35 U.S.C. 154(b) by 0 days.

(21) Appl. No.: 09/634,080

(22) Filed: Aug. 8, 2000

(51) Int. Cl.[7] ............... A61K 9/14; A61K 47/00
(52) U.S. Cl. ............ 424/486; 424/484; 424/487; 514/772.4
(58) Field of Search ................ 424/487, 486, 424/484; 514/772.4

(56) References Cited

U.S. PATENT DOCUMENTS 4,923,898    5/1990    Sunshine et al. ............ 514/557

OTHER PUBLICATIONS

Schwarz; Pharm Res May 1995; 12 (5): 687–92 Abstract.
Friedman DI; J Pharm Sci Mar. 1995; 84 (3) 324–9 Abstract.
Ranade VV; J Clin Pharmacol May 1991; 31 (5) :401–18 Abstract.
Seth PL; Arzneimittelforschung; Aug. 1993; 43 (8) :919–21 Abstract.
Schwarz JS; Pharm Res May 1995; 12 (5) :687–92 Abstract.
Friedman DI; J Pharm Sci Mar. 1995; 84 (3) :324–9 Abstract.

*Primary Examiner*—Thurman K. Page
*Assistant Examiner*—Rachel M. Bennett
(74) *Attorney, Agent, or Firm*—Welsh & Katz, Ltd.

(57) ABSTRACT

Disclosed is a local skeletal muscle relaxant and a non-steroidal anti-inflammatory drug in a topical composition for topical application to a patient for relief of pain. More particularly and in its preferred form, the invention involves a combination of diazepam and diclofenac in a composition for topical application to the skin of a patient as a colorless transparent gel.

10 Claims, No Drawings

ANALGESIC, ANTI-INFLAMMATORY AND SKELETAL MUSCLE RELAXANT COMPOSITIONS

The present invention relates generally to a novel pharmaceutical composition matter comprising a non-steroidal anti-inflammatory drug (NSAID) in combination with a skeletal muscle relaxant, and more particularly to a topical ointment comprising a mixture of diazepam and an NSAID.

The oral ingestion of certain medications such as NSAIDs and diazepam (Valium®) is well known. The analgesic and anti-inflammatory properties of NSAIDs are also well known, as is the use of diazepam to treat symptoms of acute alcohol withdrawals, control epilepsy and to relieve muscle spasms as well as short term relief of mild to moderate anxiety. Further, studies have investigated the effectiveness of the transdermal delivery of diazepam and NSAIDs individually. It would appear that the effectiveness of the transdermal delivery depends largely on the vehicle for delivery of the drug, emulsions appearing more effective than creams.

SUMMARY OF THE INVENTION

It is therefore an object of the subject invention to provide a topical composition for relief of pain in an affected body part.

A further object to the subject invention is a combination of diazepam and diclofenac in a colorless transparent gel for application locally to an affected body part for the quick relief of pain.

These and other objects of the subject invention are obtained by the subject invention wherein there is provided a local skeletal muscle relaxant and a non-steroidal anti-inflammatory drug in a topical composition for topical application to a patient for relief of pain. More particularly and in its preferred form, the invention involves a combination of diazepam and diclofenac in a composition for topical application to the skin of a patient as a colorless transparent or translucent gel.

DETAILED DESCRIPTION OF THE INVENTION

The outstanding analgesic and anti-inflammatory properties of the non-steroidal anti inflammatory drugs compared to aspirin or acetaminophen have prompted the widespread acceptance and usage of these newer non-narcotic analgesics, as single entities, for the treatment and management of acute and chronic pain and inflammatory states, notably rheumatoid arthritis and osteoarthritis. However the utilization of these agents in topical skeletal muscle relaxant compositions has not heretofore been considered.

The non-steroidal anti-inflammatory drugs (NSAIDs) for use in the pharmaceutical compositions and methods of use of the present invention may be selected from any of the following categories:

(1) the propionic acid derivatives;
(2) the acetic acid derivatives;
(3) the fenamic acid derivatives;
(4) the biphenylcarboxylic and derivatives; and
(5) the oxicams.

Accordingly, the term "NSAID" as used herein is intended to mean any non-narcotic analgesic non-steroidal anti-inflammatory compound, including the pharmaceutically acceptable non-toxic salts thereof, falling within one of the five structural categories above but excluding aspirin, acetaminophen and phenacetin.

While some of the above-identified compounds are primarily used at the present time as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) to (4) typically contain a carboxylic acid function; however, those acids are sometimes administered in the form of their pharmaceutically acceptable salts, e.g. sodium salts.

The propionic acid derivatives for use herein include, but are not limited to, ibuprofen, naproxen benaxoprofen, naproxen sodium, flurbiprofen, fenoprofen, fenbufen, ketoprofen indoprofen, pirprofen, carprofen, oxaprozin, pranoprofen, microprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Representative members of the propionic acid group include ibuprofen, naproxen, flurbiprofen, fenbufen, fenoprofen, ibuprofen aluminum, ketoprofen, fluprofen and bucloxic acid.

Thus, "propionic acid derivatives" as defined herein are non-narcotic analgesics/non-steroidal anti-inflammatory drugs having a free $-CH(CH_3)COOH$ or $-CH_2CH_2COOH$ group (which optionally can be in the form of pharmaceutically acceptable salt group, e.g. $-CH(CH_3)COO-Na+$ or $-CH_2CH_2COO-Na+$), typically attached directly or via a carbonl function to a ring system, preferably to an aromatic ring system.

The acetic acid derivatives for use herein include, but are not limited to, indomethacin, sulindac, tolmetin, diclofenac, fenclofenac, alclofenac, ibufenac, isoxepac, furofenac, tiopinac, zidometacin, acemetacin, fentiazac, clidanac and oxepinac. Structurally related acetic acid derivatives having similar analgesic and anti-inflammatory properties are also intended to be encompassed by this group. Representative members of the acetic acid group include tolmetin, sulindac, indomethacin, diclofenac, alclofenac, fenclozic acid and ibufenac.

Thus, "acetic acid derivatives" as defined herein are non-narcotic analgesics/non-steroidal anti-inflammatory drugs having a free $-CH_2COOH$ group (which optionally can be in the form of a pharmaceutically acceptable salt group, e.g. $-CH_2COO-Na+$), typically attached directly to a ring system, preferably to an aromatic or heteroaromatic ring system. The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Representative members of the fenamic acid group include mefenamic acid, meclofenamate sodium ( meclofenamic acid, sodium salt) and flufenamic acid. The biphenylcarboxylic acid derivatives for use herein include, but are not limited to, diflunisal and flufenisal. Structurally related biphenylcaboxylic acid derivatives having similar analgesic and anti-inflammatory properties are also intended to be encompassed by this group. Representative members of this group are diflunisal and flufenisal.

The term "skeletal muscle relaxant" as used herein is intended to mean diazepam, which has skeletal muscle relaxing properties. Diazepam acts directly on skeletal muscle and on the level of the central nervous system. Diazepam blocks impulses at the intemeurons of polysynaptic reflex arcs, mainly at the level of the spinal cord. This is demonstrated by the abolishment of the diminution of the flexor and crossed extensor reflexes which possess one or more interneurons between the sensory and motor fibers.

The newer non-steroidal anti-inflammatory drugs, which differ substantially in chemical structure from aspirin, acetaminophen and phenacetin, and which have significantly different biological profiles therefrom can be advantageously formulated into a novel composition together with diazepam and topically administered to mammals, especially to humans, to obtain more directed pain relief and lessened adverse side effects.

In accordance with the practices of the present invention, the NSAID/diazepam compositions may be administered in admixture with suitable pharmaceutical diluents, carrier or other excipients (collectively referred to as "carrier" materials) suitably selected with respect to the intended route of administration and conventional pharmaceutical practices. For instance, for topical administration in the form of a cream or ointment, the active drug components may be combined with any non-toxic pharmaceutically acceptable inert carrier such as a carbomer or other thickener and emulsifier.

A carbomer resin is an acrylic acid polymer, and more specifically comprises a water-swellable, but water-insoluble, fibrous, cross-linked carboxy-functional polymer. The polymer contains (a) a plurality of repeating units of which at least about 80 percent contain at least one carboxyl functionality and (b) about 0.05 to about 2.5 percent cross-linking agent substantially free from polyalkenyl polyether, with the percentages being based upon the weights of unpolymerized repeating unit and cross-linking agent, respectively. In more preferred practice, at least about 90 percent of the repeating units contain at least one carboxyl functionality, and in still more preferred practice, at least 95 percent of those repeating units contain at least one carboxyl functionality. Most preferably, the thickener is a reaction product of the polymerization of only a carboxyl-functional monomer and the cross-linking agent. Also in more preferred practice, the thickener contains about 0.1 to about 2 percent by weight of polymerized cross-linking agent.

As noted previously, at least about 80 percent of the repeating units of the thickener contain at least one carboxyl functionality. Exemplary monomers that provide these repeating units are monoethylenically unsaturated and include acrylic acid, methacrylic acid, fumaric acid, maleic acid, maleic anhydride which may be hydrolyzed in its acid form during or after polymerization, itaconic acid, crotonic acid, and the like. Each of these acids may be used alone or in combination with other such acids or with one or more pharmaceutically or cosmetically acceptable salts of those acids. Acrylic acid is a particularly preferred monomer for providing the repeating units of the thickener.

The thickeners of this invention are cross-linked by cross-linking agents as are known in the art. The cross-linking agent is substantially free from polyalkenyl polyethers, and is particularly free from polyalkenyl polyethers such as polyallyl sucrose or polyallyl pentaerythritol containing an average of at least three allyl groups per molecule as are reportedly present in CARBOPOL® 934P. Exemplary of useful cross-linking agents are divinylbenzene, N,N-diallylacrylamide, 3,4-dihydroxy-1,5-hexadiene, 2,5-dimethyl-1,5-hexadiene, and the like.

The amount of cross-linking of the thickener is of some import. When less than about 0.05 weight percent of an appropriate cross-linking agent is present, the thickener tends to become water-soluble, or water dispersible, thereby losing its desired water-insoluble, water-swellable, fibrous character that is important to the invention. When greater than about 1 percent cross-linking agent is present, the water-swellability of the thickener begins to decrease appreciably. At cross-linking agent levels greater than about 2.5 percent, the water-swellability is sufficiently decreased so as to make the thickener lose its desired, functional characteristics.

The above amounts of carboxy-functional repeating units and cross-linking agent are used to define the thickener, but specifically refer to the percentages of those predecessor, unpolymerized monomers in the reaction mixture from which the thickener is polymerized. These pre-polymerization amounts are utilized because of the great difficulty in analyzing the polymerized thickener. Although the amounts refer to the pre-polymerized monomers, it is believed that the thickeners contain substantially similar amounts of those monomers in polymerized form.

A polymer useful herein may thus be defined as a reaction product of the copolymerization of at least 80 weight percent monoethylenically unsaturated carboxy-functional monomer and about 0.05 to 1.5 weight percent of a cross-linking agent free of polyalkenyl polyether. The remaining monomers that may be present to constitute 100 percent by weight of the monomers are discussed below.

In addition to the above two ingredients, the polymer may also include polymerized monoethylenically unsaturated repeating units such as $C_1$–$C_6$ alkyl esters of one or more of the above-described acids such as hexyl acrylate, butyl methacrylate and methyl crotonate; hydroxyalkylene-functional esters of the above-described acids that contain a per molecule average of 1 to about 4 oxyalkylene groups containing 2–3 carbon atoms such as hydroxyethyl methacrylate, hydroxypropyl acrylate and tetraethylene glycol monoacrylate; methacrylamide, acrylamide and their $C_1$–$C_4$ mon- and di-alkyl derivatives such as N-methyl acrylamide, N-butyl methacrylamide and N,N-dimethyl acrylamide; styrene; and the like as are known in the art as being copolymerizable with the above-described carboxyl functionality-containing monomers and cross-linking agents. The thickener polymers most preferably are prepared from only the monoethylenically unsaturated carboxy-functional monomer and the cross-linking agent.

Other suitable thickeners include starch, gelatin, natural sugars, corn sweeteners, natural and synthetic gums such as acacia, sodium alginate, carboxymethyl-cellulose, polyethylene glycol and waxes. Suitable emollients and emulsifiers should be added for skin care and reducing surface tension n the mixture. Fragrances and flavoring agents and preservatives can also be included were appropriate.

Suitable emollients are vegetable or caprylic/capric acid ester of saturated fatty alcohol ($C_{16}$–$C_{18}$) (available as Cetiol LC from Henkel Canada, Ltd.) in the amount of 1.5% to 3.5%. Other suitable emollients are fatty acid esters, fatty alcohols, oils, dexpanthenol and other such chemicals with lipophilic characteristics.

A suitable emulsifier is polyoxyethylene (20) ceto stearyl ether in the amount of 1.0% to 3.0% Other suitable emulsifiers are ionic, amphoteric surfactants derived from synthetic or natural sources with a HLB value suitable for emulsification purpose.

Sufficient amounts of a pharmaceutically acceptable neutralizing base is added to bring the acidity down to slightly on the basic side (pH=7–8). One such acceptable base is Diethylamine in the amount of 0.5% to 3.0%. Other suitable bases are $NH_3OH$, other ammonia based compounds, other compounds containing a hydroxyl group or nitrogen containing bases.

EXAMPLE 1
Product: Diazepam 1% and Diclofenac Sodium 1% Gel

| Ingredients | g/100 g |
| --- | --- |
| Carbopol 934P (B. F. Goodrich) | 1.200 |
| Purified Water (75° C.–80° C.) | 55.641 |
| Liquid Paraffin | 2.500 |
| Cetiol LC (Henkel Canada, Ltd.) | 2.500 |
| Cetomacrogol 1000 (Croda Chemicals) | 2.000 |
| Diethylamine | 0.900 |
| Purified Water (75° C.–80° C.) | 5.000 |
| Isopropyl Alcohol (40° C.–45° C.) | 23.000 |
| Propylene Glycol | 5.000 |
| Diazepam | 1.000 |
| Diclofenac Diethylamine | 1.160 |
| Lavender Oil | 0.028 |
| Rose Oil | 0.071 |

Procedure

1. Disperse Carbopol 934P in Purified Water (75° C.–80° C.). Cool to 30° C. –35° C.
2. Melt Cetomacrogol 1000, Liquid Paraffin, Cetiol LC at 70° C. Cool to 30° C.–35° C.
3. Add step 1 into step 2. Mix well.
4. Dissolve Diethylamine in Purified Water (25° C.–30° C.). Add in to step 3. Mix and homogenize.
5. Dissolve Diazepam and Diclofenac Diethylamine in the mixture of Isopropyl Alcohol and Propylene Glycol (40° C.–45° C.). Cool to 30° C.–35° C.
6. Add step 5 into step 3. Mix and homogenize well.
7. Add the flavors in step 6 and mix well.

Description: Colorless transparent gel
pH: Between 7.0 & 8.0

The above topical gel was administered to a subject by rubbing on an affected area. Relief was noted within a few minutes and lasted for a few hours. A slight systemic effect was noted.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed is:

1. A composition for topical application to a body surface, comprising:

0.5% to 2.5% carbomer

50% to 65% $H_2O$ 1.5% to 3.5% paraffin 1.5% to 3.0% emollient 1.0% to 3.0% emulsifier 0.5% to 2.0% diethylamine 0.5% to 3.0% pharmaceutically acceptable neutralizing base 20% to 30% alcohol 1.5% to 5.0% propylene glycol 0.1% to 5.0% diazepam 0.1% to 5.0% nonsteroidal anti-inflammatory drug in a homogenized mixture.

2. The composition of claim 1 wherein the carbomer is a cross-linked acrylic acid polymer.

3. The composition of claim 2 wherein the acrylic acid polymer is cross-linked with a polyalkenyl polyether.

4. The composition of claim 1 wherein the emollient is a caprylic acid ester of a saturated fatty alcohol (C=16 to 18).

5. The composition of claim 1 wherein the emulsifier is polyoxyethylene ceto stearyl ether.

6. The composition of claim 1 wherein the pharmaceutically acceptable neutralizing base is diethyl amine.

7. The composition of claim 1 wherein the alcohol is isopropyl alcohol.

8. The composition of claim 1 wherein the nonsteroidal anti-inflammatory drug is diclofenac diethylamine.

9. A homogenized composition for topical application to a skin surface including:

1.2% cross-linked acrylic acid polymer 60.64% water 2.5% paraffin 2.5% caprylic acid ester of a saturated fatty alcohol 2.0% polyoxyethylene ceto stearyl ether 0.9% diethyl amine 23.0% isopropyl alcohol 5.0% propylene glycol 1.0% diazepam 1.15% diclofenac diethylamine 0.1% fragrances.

10. The composition of claim 9 wherein the acrylic acid polymer is cross-linked with a polyalkenyl polyether.

* * * * *